United States Patent [19]
Ritzer et al.

[11] Patent Number: 6,160,160
[45] Date of Patent: Dec. 12, 2000

[54] PROCESS FOR PREPARING BENZYL CARBAZATES

[75] Inventors: Edwin Ritzer; Robert Söllner, both of Leverkusen; Claus Dreisbach, Köln; Frank Jelitto, Bergisch Gladbach, all of Germany

[73] Assignee: Bayer Aktiengesellschaft, Leverkusen, Germany

[21] Appl. No.: 09/369,818

[22] Filed: Aug. 6, 1999

[30] Foreign Application Priority Data

Aug. 17, 1998 [DE] Germany .................. 198 37 070

[51] Int. Cl.⁷ .................................................. C07C 261/00
[52] U.S. Cl. ............................................. 560/159; 560/169
[58] Field of Search ................................. 56/159

[56] References Cited

U.S. PATENT DOCUMENTS

| | | | |
|---|---|---|---|
| 4,734,119 | 3/1988 | Diel et al. | 71/86 |
| 4,739,093 | 4/1988 | Diel et al. | 558/154 |
| 5,159,099 | 10/1992 | Romano et al. | 558/277 |
| 5,756,824 | 5/1998 | Landscheidt et al. | |

FOREIGN PATENT DOCUMENTS 0 106 282   4/1984   European Pat. Off. .

OTHER PUBLICATIONS

Journal of Biological Chemistry, vol. 266, Mar. 25, 1991, pp. 5525–5533.
Chem. Ber., 92 (month unavailable) 1959, pp. 1478–1480.
Journal of the American Chemical Soc., vol. 70, Feb.–Mar. 1948, pp. 1181–1183.
Ber. Chem. Ges. 47, (month unavailable) 1914, pp. 2183–2195.
M. Selva et al, "Selective mono–benzylation of methylene active compounds with debenzyl carbonate: benzylation of phenol", Journal Chem. Soc. Perkin Trans. 1 Bd. 15 1995, pp. 1889–1894, XP002124351.

*Primary Examiner*—Paul J. Killos
*Assistant Examiner*—Sherif Kafafi
*Attorney, Agent, or Firm*—Joseph C. Gil; Richard E. L. Henderson

[57] ABSTRACT

The present invention relates to a process for preparing optionally substituted benzyl carbazates of formula (I)

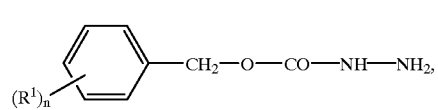

wherein each $R^1$ independently represents $C_1$–$C_4$-alkyl, $C_1$–$C_4$-alkoxy, di($C_1$–$C_4$-alkyl)amino, nitro, halogen, hydroxyl, the group X-$R^3$, wherein X represents O or S and $R^3$ represents straight-chain or branched $C_1$–$C_4$-alkyl, the group COO$R^4$, wherein $R^4$ represents $C_1$–$C_4$-alkyl, the group N$R^5R^6$, wherein $R^5$ and $R^6$ independently represent $C_1$–$C_4$-alkyl, or a $C_3$–$C_6$-cycloalkyl group that is optionally substituted by straight-chain or branched $C_1$–$C_4$-alkyl groups, and n is an integer from 0 to 5, by reacting a dialkyl carbonate with an optionally substituted benzyl alcohol in the presence of a catalyst, separating off the resulting reaction mixture from the catalyst, and subsequently reacting the separated reaction mixture with hydrazine hydrate.

10 Claims, No Drawings

PROCESS FOR PREPARING BENZYL CARBAZATES

BACKGROUND OF THE INVENTION

The present invention relates to a process for preparing optionally substituted benzyl carbazates by reacting $C_1$–$C_8$-dialkyl carbonates with optionally substituted benzyl alcohols in the presence of a catalyst, followed by reaction with hydrazine hydrate.

Increasingly, carbazates are being used as intermediates for preparing crop protection agents and pharmaceutics. In particular, they are employed for synthesizing peptides (European Patent Application EP 106,282). Furthermore, according to *J. Biol. Chem.*, 266, 5525 (1991), it is possible to prepare hydrazinosuccinate, an inhibitor of aspartate aminotransferase, from benzyl carbazate. European Patent Application EP 143,078 describes the use of benzyl carbazate for preparing crop protection agents. Against this background, the preparation of carbazates assumes increased importance.

In general, carbazates are obtained by reacting chloroformic esters with hydrazine. Thus, *Chem. Ber.*, 92, 1478 (1959) describes the reaction of benzyl chloroformate with hydrazine with formation of benzyl carbazate.

However, the preparation of the precursors, which is carried out using phosgene, is comparatively complex, and the purity of the resulting carbazates is insufficient for some purposes since by-products that contaminate the desired carbazate are formed during the multistep synthesis from thermally sensitive intermediates.

According to another method, symmetrical dialkyl carbonates are reacted with hydrazine. *J. Am. Chem. Soc.*, 70, 1181 (1948). Here, likewise, the preparation of the precursors is difficult or impossible, particularly for higher carbonates. Moreover, this procedure is problematic since, in the isolation of the product as a hydrochloride, the formation of chlorinated, and in some cases corrosive, compounds during work-up cannot be avoided completely.

Furthermore, European Patent Application EP 770,598 discloses a process for preparing optionally substituted $C_2$–$C_{20}$-alkyl, $C_3$–$C_6$-cycloalkyl, and $C_6$–$C_{12}$-aryl carbazates in which an unsubstituted $C_1$–$C_4$-alkyl carbazate is reacted with an optionally substituted $C_2$–$C_{20}$-alkyl, $C_3$–$C_6$-cycloalkyl, or $C_6$–$C_{12}$-aryl alcohol in the presence of a catalyst. Here, the unsubstituted $C_1$–$C_4$-alkyl carbazate can be obtained by reacting dialkyl carbonates with hydrazine. See, for example, *Ber. Chem. Ges.*, 47, 2183–2188. Whereas the purity of the resulting alkyl, cycloalkyl or aryl carbazates is good (for example, 97%), the carbazate yield of the process, based on the alkyl carbazate employed, is relatively low (for example, only about 65%).

Due to the growing demand for carbazates, particularly for benzyl carbazates, it was therefore an object to provide a technically simple process for preparing benzyl carbazates of high purity.

SUMMARY OF THE INVENTION

This object is achieved by a process for preparing optionally substituted benzyl carbazates of formula (I)

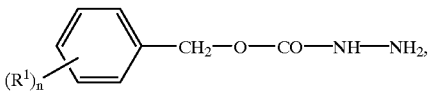

(I)

wherein
each $R^1$ independently represents $C_1$–$C_4$-alkyl, $C_1$–$C_4$-alkoxy, di($C_1$–$C_4$-alkyl)amino, nitro, halogen, hydroxyl, the group X-$R^3$, wherein X represents O or S and $R^3$ represents straight-chain or branched $C_1$–$C_4$-alkyl, the group COOR$^4$, wherein $R^4$ represents $C_1$–$C_4$-alkyl, the group NR$^5$R$^6$, wherein $R^5$ and $R^6$ independently represent $C_1$–$C_4$-alkyl, or a $C_3$–$C_6$-cycloalkyl group that is optionally substituted by straight-chain or branched $C_1$–$C_4$-alkyl groups, and
n is an integer from 0 to 5,
comprising
(1) reacting, in a first reaction step,
   (a) a dialkyl carbonate of formula (II)

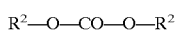

(II)

wherein $R^2$ represents a branched or unbranched $C_1$–$C_8$-alkyl radical,
   (b) a benzyl alcohol of formula (III)

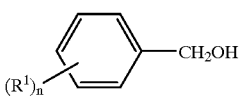

(III)

wherein $R^1$ and n are defined as for formula (I), and
   (c) a catalyst to form a reaction mixture;
(2) separating the reaction mixture from the catalyst; and
(3) reacting, in a second reaction step, the resultant separated reaction mixture with hydrazine hydrate.

DETAILED DESCRIPTION OF THE INVENTION

In the dialkyl carbonate of the formula (II) used in the first step of the process, $R^2$ represents a branched or unbranched $C_1$–$C_8$-, preferably $C_1$–$C_4$-alkyl radical, in particular methyl or ethyl.

Such dialkyl carbonates are easily accessible. Dimethyl carbonate, for example, can be prepared on an industrial scale without using phosgene by oxidation of carbon monoxide with oxygen in the presence of methanol and catalysts. European Patent Application EP 365,083.

In the benzyl alcohols of the formula (III), the benzyl ring is optionally substituted by one or more radicals $R^1$, where each $R^1$ is identical or different and represents $C_1$–$C_4$-alkyl (preferably $C_1$–$C_3$-alkyl), $C_1$–$C_4$-alkoxy (preferably $C_1$–$C_3$-alkoxy), di($C_1$–$C_4$-alkyl)amino (preferably di($C_1$–C3-alkyl) amino), nitro, halogen, hydroxyl, the group X-$R^3$ (where X represents O or S and $R^3$ represents straight-chain or branched $C_1$–$C_4$-alkyl), the group COOR$^4$ (where $R^4$ represents $C_1$–$C_4$-alkyl), the group NR$^5$R$^6$ (where $R^5$ and $R^6$ independently represent $C_1$–$C_4$-alkyl), or a $C_3$–$C_6$-cycloalkyl group that is optionally substituted by straight-chain or branched $C_1$–$C_4$-alkyl groups, and n is an integer from 0 to 5 (preferably from 0 to 3, particularly 0 or 1).

Suitable catalysts for use in the first step of the process according to the invention are various basic compounds. For reasons of easier separability after the process according to the invention has ended, solid basic compounds are preferred for use as catalysts. Examples of suitable catalysts include alkali metal hydroxides, such as lithium hydroxide, sodium hydroxide and potassium hydroxide; alkaline earth metal carbonates and bicarbonates, such as lithium carbonate, sodium carbonate, potassium carbonate, magnesium carbonate, calcium carbonate, sodium bicarbonate, and potassium bicarbonate; and alkali metal and alkaline earth metal alkoxides, such as lithium methoxide and sodium methoxide. Preference is given to alkali metal carbonates, particularly sodium carbonate. When using alkali metal and alkaline earth metal alkoxides, preference is given to those derived from the alcohol of the formula (III) employed in each case in order to avoid the formation of undesirable by-products.

The catalyst is usually employed in an amount of from 0.1 to 10% by weight (preferably from 0.5 to 5% by weight, particularly from 1 to 3% by weight), based on the dialkyl carbonate of the formula (II).

If appropriate, the reaction of the dialkyl carbonates of the formula (II) with the benzyl alcohols of the formula (III) in the first step is carried out in the presence of an organic solvent that is stable under the chosen reaction conditions and inert towards the dialkyl carbonates and benzyl alcohols employed and the resulting dibenzyl carbonates.

These organic solvents may be hydrocarbons, ethers, and acid amides, such as cyclohexane, toluene, chlorobenzene, ethylene glycol dimethyl ether, diethylene glycol dimethyl ether, and dimethylformamide.

For carrying out the first step of the process according to the invention, the dialkyl carbonate of the formula (II) and the benzyl alcohol of the formula (III) are employed in a molar ratio of from 1:1 to 8:1 (preferably 1.5:1 to 6:1 and particularly 2:1 to 4:1).

The first step of the process is usually carried out at temperatures of from 60 to 160° C. (preferably from 80 to 140° C.) and a pressure of from 0.0001 to 0.1 MPa (i.e., 0.001 to 1 bar).

The alcohol $R^2$-OH formed during the first step is preferably already distilled off during the reaction. This process can be promoted by the solvent used in the first step, for example, an aromatic hydrocarbon (particularly toluene) that forms an azeotrope with the alcohol $R^2$-OH.

If appropriate, the pressure can be reduced to below 0.0001 MPa (1 mbar) toward the end of the reaction in the first step.

After the first step has ended, the reaction mixture is worked up by separating the catalyst, for example, by sedimentation, filtration, or extraction with water. Any excess benzyl alcohol or excess dialkyl carbonate that may still be present can be separated, if appropriate, by distillation. The remaining crude reaction product can be used directly for the reaction of the second step or else purified beforehand by an additional distillation step.

In the second step of the process according to the invention, the reaction mixture of the first step is reacted with hydrazine hydrate. It has been found to be advantageous to operate at temperatures of from 60 to 160° C. (preferably from 80 to 140° C.) and at a pressure of from 0.01 to 1 MPa (i.e., 0.1 to 10 bar) (preferably 0.1 MPa (i.e., 1 bar)). The addition of a catalyst in this second step is not necessary.

The hydrazine hydrate is employed in a molar ratio of 1:1 to 3:1 (preferably 1:1 to 2:1), based on the dibenzyl carbonate. The alcohol $R^2$OH that forms during the second step is, analogously to the first step, already distilled off during the reaction, particularly in the form of an azeotrope with an aromatic hydrocarbon, such as toluene, that is present as solvent. Additionally or alternatively, the pressure can be lowered to below $10^{-4}$ MPa (i.e., 1 mbar) toward the end of the reaction in the second step.

After the reaction has ended in the second step, the reaction mixture can be worked-up with known techniques, for example, by distillation (particularly steam distillation) or by crystallization (particularly solution or melt crystallization).

By employing the process according to the invention, it is possible to provide the desired, optionally substituted benzyl carbazates in a technically simple manner. It is not necessary to use chemicals that are difficult to handle and wastes for which disposal is costly are not produced. Furthermore, the process is distinguished in that the desired benzyl carbazates are obtained in high purity, i.e., free of by-products that cannot be removed or which are difficult to remove and that interfere in subsequent reactions. It is particularly important to obtain benzyl carbazate products that are chloride-free and thus non-corrosive. Apart from exceptional cases, further purification of the benzyl carbazates prior to their use in subsequent reactions is, therefore, not required.

A further advantage consists in the gentle reaction conditions of the process, due to which it is possible to prepare even heat-sensitive benzyl carbazates.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1 Preparation of benzyl carbazate

1st Step: Dibenzyl carbonate from diethyl carbonate

At room temperature, 472 g (4.0 mol) of diethyl carbonate, 864 g (8.0 mol) of benzyl alcohol, and 8 g of sodium carbonate are mixed. With stirring, the reaction mixture is heated to the boil and the ethanol that is formed is distilled off to bring the reaction to completion. During this process, the bottom temperature increases to 140° C. When no more alcohol distills off, the pressure is reduced while the bottom temperature is kept constant.

Once a pressure of $10^{-4}$ MPa (1 mbar) at 140° C. has been reached, these conditions are maintained for another hour. The mixture is subsequently cooled and the catalyst is separated by sedimentation and filtration. The reaction mixture which remains after removal of the catalyst is subsequently purified distillatively, giving 855 g of dibenzyl carbonate, 24.4 g of diethyl carbonate, 260 g of ethanol, 183.1 g of benzyl alcohol, 14.8 g of benzyl ethyl carbonate, and 0.17 g of dibenzyl ether.

2nd Step: Preparation of benzyl carbazate from dibenzyl carbonate Experiment A:

At room temperature, 2556 g (10.6 mol) of dibenzyl carbonate and 575 g (17.8 mol) of hydrazine hydrate are mixed. With stirring, the reaction mixture is heated to boiling and the benzyl alcohol that is formed is distilled off together with the water to bring the reaction to completion. During this process, the bottom temperature increases to 140° C. When no more alcohol distills off, the pressure is reduced while the bottom temperature is kept constant.

Once a pressure of $10^{-4}$ MPa (1 mbar) at 140° C. has been reached, these conditions are maintained for another hour. The mixture is subsequently cooled and the product is worked up distillatively. The distillation residue of 1600 g has the following composition: 97% benzyl carbazate (a yield of 88.2%, based on the dibenzyl carbonate employed). 0.37% benzyl alcohol, 0.16% dibenzyl ether, and 0.32% dibenzyl carbonate. Experiments B, C, and D:

The 2nd step is carried out analogously in further experiments B, C, and D at room temperature using the dibenzyl carbonate and hydrazine hydrate ratios given in Table 1. The amount and purity of benzyl carbazate that is obtained are likewise summarized in Table 1.

TABLE 1

| Experiment | Dibenzyl carbonate (g) | Hydrazine hydrate (g) | Bottom temperature (° C.) | Benzyl carbazate (g) | Purity (%) |
|---|---|---|---|---|---|
| B | 126.5 | 27.5 | 160 | 83 | 92.3 |
| C | 563.3 | 165 | 165 | 391 | 73.8 |
| D | 512.7 | 120 | 123 | 386 | 82.6 |

The distillation residue can be further worked up by the methods described below.

I. Purification by Recrystallization from Diethyl Carbonate

At room temperature, 100 g of benzyl carbazate from experiment A (97% pure) and 50 g of diethyl carbonate are mixed and the mixture is heated to 70° C. The mixture is then cooled and seeded. After crystallization, separation, and drying under reduced pressure at 40° C., 52 g of benzyl carbazate of a purity greater than 99.5% are obtained.

II. Purification by Melting in the Presence of Water

At room temperature, 100 g of benzyl carbazate from experiment A (97% pure) and 100 g of water are mixed and the mixture is heated to 90° C. The mixture is then cooled to 40° C. After solidification and drying under reduced pressure at 40° C., 94 g of benzyl carbonate having a purity of more than 99.5% are obtained.

III. Purification by Melt Crystallization

The bottom of a two-inch long glass tube fitted with a thermostat mantle is closed with a stopper and the tube is heated to 80° C. The tube is then filled with molten crude benzyl carbazate. The tube is closed with a second stopper through which a Pt100 thermoelement is led. Within 30 minutes, the charge is cooled to its solidification point and the heat of solidification is dissipated completely. Within 60 min, the material is then cooled to 10° C. below the solidification point and the moment at which T (internal) and T (heating mantle) are the same is awaited. By removing the bottom stopper, the fraction of the product mixture that is still liquid (waste liquor) is separated. The waste liquor contains carbonic acid dihydrazide which, after re-melting, no longer melts and can be separated off by filtration.

By slowly heating the tube, a further fraction (sweat fraction) becomes molten and is separated. This intermediate liquor corresponds approximately to the material that is charged and it can be melted into the next pure fraction and be obtained as a melt. By using appropriate temperature programs, the second pure crystallization or the waste liquor crystallization can be carried out, giving 83 g of benzyl carbazate of a purity of more than 99.0%.

IV. Purification by Steam Distillation

At room temperature, 100 g of benzyl carbazate from experiment A (97% pure) and 20 g of water are mixed and the mixture is heated to 70° C. Under reduced pressure (20 mbar), the water is subsequently distilled off together with the volatile organic substances. The bottom subsequently crystallizes out, giving 96 g of benzyl carbazate of a purity of more than 99.0%.

What is claimed is:

1. A process for preparing optionally substituted benzyl carbazates of formula (I)

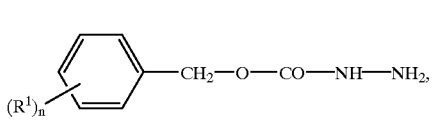

(I)

wherein each $R^1$ independently represents $C_1$–$C_4$-alkyl, $C_1$–$C_4$-alkoxy, di($C_1$–$C_4$-alkyl)amino, nitro, halogen, hydroxyl, the group X-$R^3$, wherein X represents O or S and $R^3$ represents straight-chain or branched $C_1$–$C_4$-alkyl, the group COO$R^4$, wherein $R^4$ represents $C_1$–$C_4$-alkyl, the group N$R^5R^6$, wherein $R^5$ and $R^6$ independently represent $C_1$–$C_4$-alkyl, or a $C_3$–$C_6$-cycloalkyl group that is optionally substituted by straight-chain or branched $C_1$–$C_4$-alkyl groups, and n is an integer from 0 to 5, comprising (1) reacting, in a first reaction step,
  (a) a dialkyl carbonate of formula (II)

(II)

wherein $R^2$ represents a branched or unbranched $C_1$–$C_8$-alkyl radical, (b) a benzyl alcohol of formula (III)

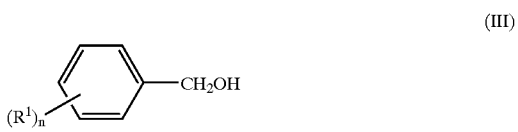

(III)

wherein $R^1$ and n are defined as for formula (I), and
  (c) a catalyst to form a reaction mixture;

(2) separating the reaction mixture from the catalyst; and (3) reacting, in a second reaction step, the resultant separated reaction mixture with hydrazine hydrate.

2. A process according to claim 1 wherein in the dialkyl carbonates of formula (II) $R^2$ represents a branched or unbranched $C_1$–$C_4$-alkyl radical.

3. A process according to claim 1 wherein in the benzyl alcohols of the formula (III) $R^1$ represents $C_1$–$C_3$-alkyl, $C_1$–$C_3$-alkoxy, di($C_1$–$C_3$-alkyl)amino, or chlorine, and n is an integer from 0 to 3.

4. A process according to claim 1 wherein the catalyst is an alkali metal carbonate.

5. A process according to claim 1 wherein the catalyst is employed in an amount of from 0.1 to 10% by weight, based on the dialkyl carbonate of formula (II).

6. A process according to claim 1 wherein the first step is carried out at a temperature of from 60 to 160° C. and at a pressure of from 0.0001 to 0.1 MPa.

7. A process according to claim 1 wherein in the first step of the process the dialkyl carbonate of the formula (II) and the benzyl alcohol of the formula (III) are employed in a molaf ratio of 1:1 to 8:1.

8. A process according to claim 1 wherein the second step is carried out at a temperature of from 60 to 160° C. and a pressure of from 0.01 to 1 MPa.

9. A process according to claim 1 wherein in the second step the hydrazine hydrate is employed in a molar ratio of 1:1 to 3:1, based on the dibenzyl carbonate.

10. A process according to claim 1 wherein the reaction mixture is worked up by distillation or crystallization after completion of the second step.

* * * * *